US006813960B1

(12) United States Patent
Owen et al.

(10) Patent No.: US 6,813,960 B1
(45) Date of Patent: Nov. 9, 2004

(54) ASYMMETRICAL COLUMN ASSEMBLY FOR HIGH-CYCLE FATIGUE TEST MACHINES

(75) Inventors: Thomas E. Owen, Helotes, TX (US); David L. Davidson, San Antonio, TX (US); John B. Campbell, San Antonio, TX (US); Andrew Nagy, deceased, late of San Antonio, TX (US); by Madeline M. Nagy, legal representative, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 10/223,567

(22) Filed: Aug. 19, 2002

(51) Int. Cl.$^7$ ............................. G01N 3/32; G01N 3/00
(52) U.S. Cl. ............................ 73/808; 73/794
(58) Field of Search ........................ 73/808, 794, 83, 73/7

(56) References Cited

U.S. PATENT DOCUMENTS

| | | | |
|---|---|---|---|
| 2,788,659 A | 4/1957 | Radnar at al. ............... 73/67.4 |
| 3,269,175 A | 8/1966 | Sprosty ....................... 73/141 |
| 3,470,400 A | 9/1969 | Weisbord ..................... 310/19 |
| 3,479,536 A | 11/1969 | Norris ......................... 310/8.5 |
| 3,563,086 A | 2/1971 | Reed, Jr. ....................... 73/92 |
| 3,690,162 A | 9/1972 | Stecher ......................... 73/797 |
| 4,355,538 A | 10/1982 | Hall ............................. 73/811 |
| 4,372,173 A | 2/1983 | EerNisse et al. .......... 73/862.59 |
| 4,523,121 A | 6/1985 | Takahashi et al. ........... 310/334 |
| 4,546,658 A | 10/1985 | Rocha et al. ............ 73/862.59 |
| 4,637,259 A | 1/1987 | Jones ........................... 73/791 |
| 4,667,127 A | 5/1987 | Krempl et al. .............. 310/338 |
| 4,686,860 A | 8/1987 | Liu ............................. 73/856 |
| 4,748,854 A | 6/1988 | Rao ............................. 73/799 |
| 4,869,111 A | 9/1989 | Ohya et al. ................... 73/811 |
| 4,869,112 A | 9/1989 | Gram et al. ................... 73/796 |
| 5,375,451 A | 12/1994 | Sandstrom ...................... 73/7 |
| 5,388,464 A | 2/1995 | Maddison ..................... 73/856 |
| 5,425,276 A | 6/1995 | Gram et al. ................... 73/816 |
| 5,442,964 A | 8/1995 | Coates et al. ............ 73/862.68 |
| 5,528,942 A | 6/1996 | Baratta ........................ 73/856 |
| 5,581,040 A | 12/1996 | Lin ............................. 73/856 |
| 5,677,494 A | * 10/1997 | Keener et al. ................ 73/810 |
| 6,023,980 A | * 2/2000 | Owen et al. .................. 73/797 |
| 6,601,456 B1 | 8/2003 | Davidson et al. ............. 73/808 |

FOREIGN PATENT DOCUMENTS

| | | | |
|---|---|---|---|
| DE | 3818831 | 12/1989 | ............ G01N/3/32 |
| GB | 2137024 | 9/1984 | ............. B06B/1/06 |

OTHER PUBLICATIONS

International Search Report PCT/US 98/03209, mailed Jun. 22, 1998.
Lee et al., "*Electrohydraulic Fatigue Apparatus for Testing in Ultrahigh Vacuum and Controlled Environments*", Review of Scientific Instruments, vol. 57, No. 11 pp. 2854–2858, Nov. 1986.
Hoffelner, "*Fatigue Crack Growth at 20 kHz—A New Technique*", Journal of Physics, vol. 37, No. 6, pp. 617–619, Jun. 1990.

\* cited by examiner

Primary Examiner—Edward Lefkowitz
Assistant Examiner—Lilybett Martir
(74) Attorney, Agent, or Firm—Baker Botts L.L.P.

(57) ABSTRACT

A column assembly for use in conjunction with a test machine, for inducing high-cycle fatigue (at kilohertz vibration rates) in a specimen of a material under test. The column assembly has isolation masses, a specimen grip, and two actuators, the latter for imparting dynamic forces to the test specimen. The actuators are arranged on the column assembly asymmetrically relative to the test specimen.

16 Claims, 2 Drawing Sheets

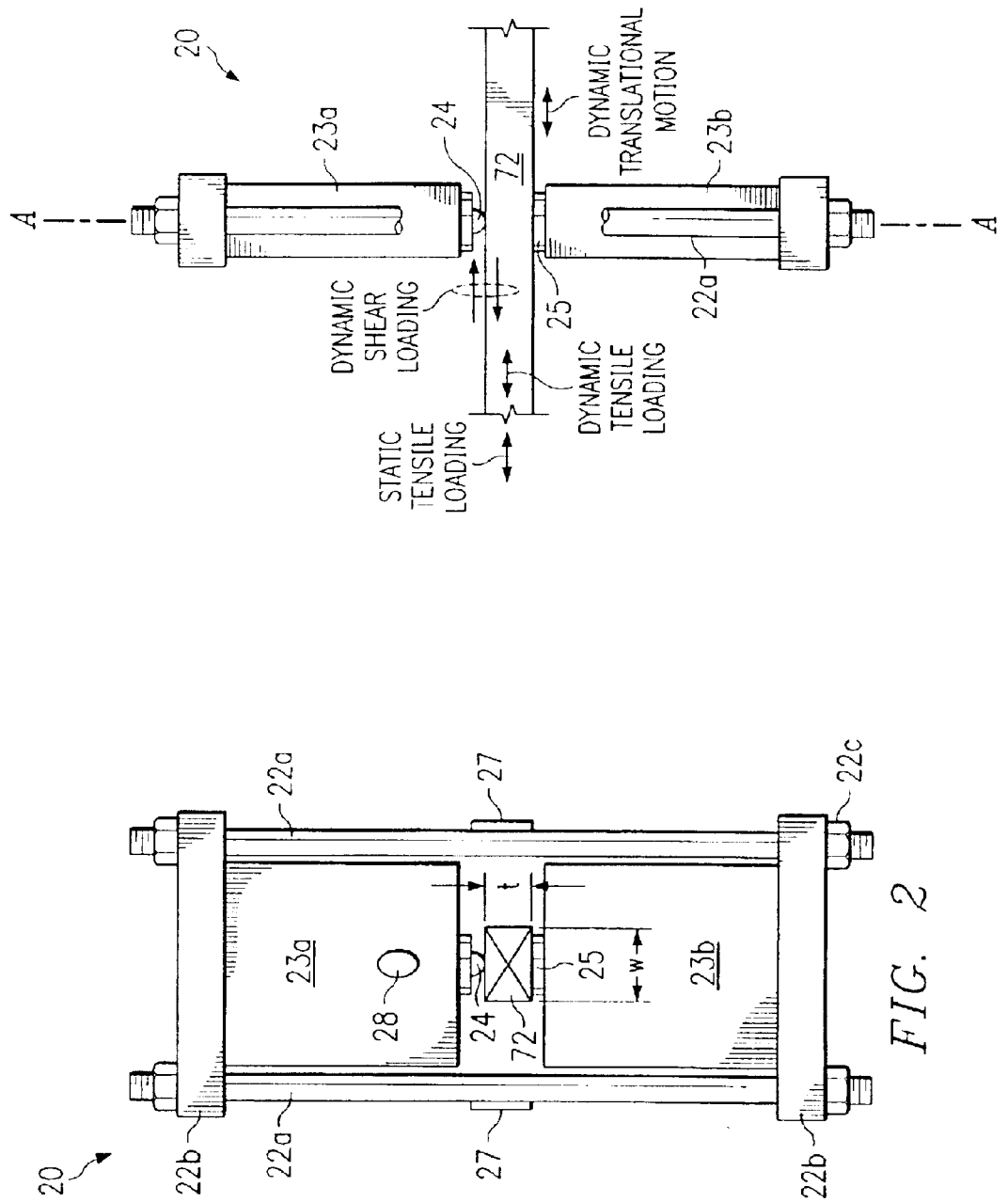

ASYMMETRICAL COLUMN ASSEMBLY FOR HIGH-CYCLE FATIGUE TEST MACHINES

TECHNICAL FIELD OF THE INVENTION

The present invention relates generally to equipment for testing physical characteristics of materials, and more specifically, to a column assembly for a test machine that enables the machine to subject a sample of material to high-cycle stress.

BACKGROUND OF THE INVENTION

High-cycle fatigue (HCF) is so-called because it appears after millions of repetitive cycles of stressful vibrations or other use, which can affect even high-strength metals such as the titanium alloys used in the gas turbines that power aircraft. These materials and components must endure repeated, long-term exposure to high temperatures and static and dynamic stresses caused by rotation speeds of 7,000 to 10,000 revolutions per minute. Under these conditions, blade and disk materials must be able to withstand a large number of stress cycles. Fatigue cracks can initiate and grow at stress levels that are low in relation to the material's yield stress. And, because of the very large number of cycles involved, laboratory study of HCF failure phenomena must be carried out at high frequencies to characterize the behavior of cracks within reasonable time limits.

U.S. Pat. No. 6,023,980, to Thomas E. Owen, et al., entitled "High-Cycle Fatigue Test Machine", describes embodiments of a test machine that may be used to statically and dynamically load a test specimen in a manner that introduces controlled cyclic fatigue forces at high vibrational rates. In one embodiment, the test machine combines a high-frequency machine with a scanning electron microscope (SEM). This SEM-compatible test machine applies stress to a test specimen by two means. A steady stress is applied by hydraulic pressure. At the same time, high-frequency dynamic stresses are applied by piezoceramic actuators that cause the machine as well as the specimen to resonate between 1,000 to 1,700 cycles per second. The resonance condition amplifies the dynamic loading generated by the piezoceramic actuators and is an important design feature of the machine. Static loads of up to 6,000 pounds, and dynamic loads of up to ±1,200 pounds, can be applied to a specimen.

In another embodiment described in U.S. Pat. No. 6,023,980, a column assembly is used with a conventional tensile testing machine to create the high-cycle forces. In particular, a laboratory test machine arrangement is described, in which an isolation mass, a dynamic actuator, and a specimen coupler are placed on both ends of a specimen. The specimen is mounted between opposing faces of the couplers. The result is a column assembly that is symmetrical on either side of the specimen. When mounted in a tensile testing machine, the column may be placed in tension to produce a desired static tensile stress in the specimen. The dynamic actuators may then be excited to produce axially oriented mechanical vibration resonances in the column assembly.

BRIEF DESCRIPTION OF THE DRAWINGS

FIG. 2 illustrates the fretting fixture of FIG. 1.

FIG. 3 is a side view of the fretting fixture.

DETAILED DESCRIPTION OF THE INVENTION

Figure 1:
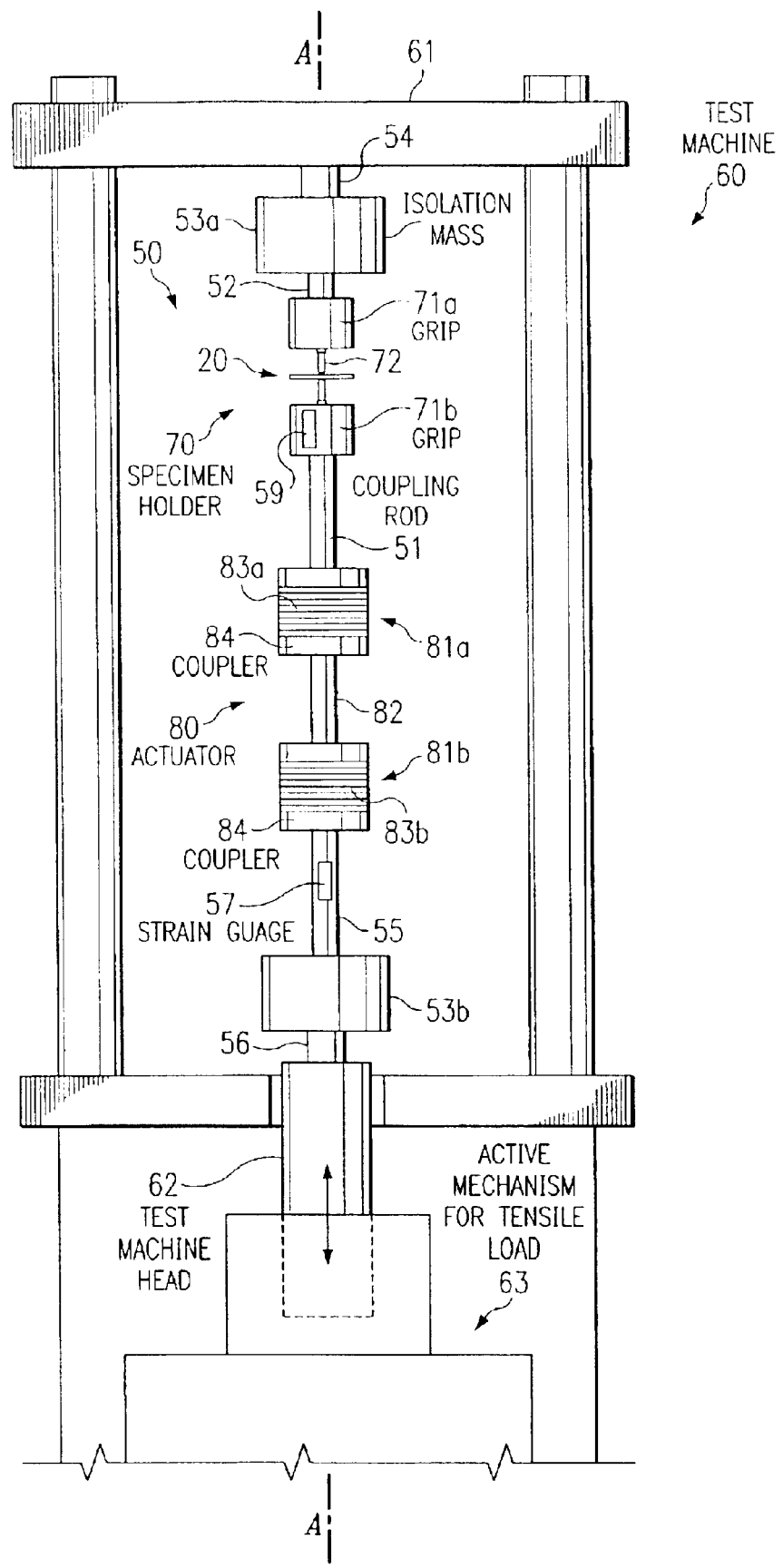
FIG. 1 illustrates a column assembly for a fatigue test machine, in accordance with the invention.

FIG. 1 illustrates a columnar testing assembly 50 for producing high-cycle fatigue in test specimens. Assembly 50 is operated in conjunction with a conventional materials tensile testing machine 60 capable of producing a static tensile loading force on a specimen 72. Column assembly 50 is suitable for mounting on a number of commercially available tensile testing machines.

In the example of FIG. 1, column assembly 50 is shown with a fretting fixture 20 clamped to specimen 72, as explained below in connection with FIGS. 2 and 3. However, if desired, column assembly 50 may be used without fretting fixture 20 to produce high-cycle fatigue, or with other types of stress-inducing fixtures.

Column assembly 50 consists of a specimen holder unit 70 comprised of two specimen grips 71a and 71b for holding the ends of a test specimen 72, and a dynamic actuator unit 80 comprised of two piezoelectric actuators 81a and 81b joined together by a compliant coupling bar 82. One end of the specimen holder unit 70, for example, the grip component 71b, is attached to one end of the dynamic actuator unit 80, for example, actuator component 81a, by a stiff coupling rod 51. Vibrations of dynamic actuator unit 80 are transferred to the specimen holder unit 70 and, in turn, to the test specimen 72 by the coupling rod 51. The opposite (upper) end of specimen holder unit 70, for example, grip component 71a, is attached to a vibration isolation mass 53a by a stiff coupling rod 52 and isolation mass 53a, in turn, is attached to the stationary top beam 61 of test machine 60 by a stiff coupling rod 54. The opposite (lower) end of the dynamic actuator unit 80, for example, actuator component 81b, is attached to a second isolation mass 53b by a coupling rod 55. The isolation mass 53b is attached to the moveable head 62 of the test machine 60 by a stiff coupling rod 56. The active mechanism 63 of test machine 60 imparts a tensile loading force on column assembly 50 such that all of the components comprising column assembly 50 are subject to the same tensile loading force.

The opposing faces of specimen holder unit 70, that is, the faces of grip components 71a and 71b, may use various means for holding the ends of the specimen. Typically, specimen 72 is a bar of the test material, such that each end may be easily grasped by grip component 71a or 71b, respectively.

The active mechanism 63 of test machine 60 may utilize any one of several operating methods, such as hydraulic, electromechanical, or servo-electric, to apply static mechanical tension to the column assembly 50. Downward movement of the moveable head 62 shown in FIG. 1 will apply a tensile force to column assembly 50. Most commercial testing machines appropriate for use in this intended application have built-in load cells or calibrated strain gauges by which the tensile loading force is sensed and displayed to the operator. Further, many such test machines have an input/output signal and command and control interface by which the machine may be controlled by external means. Additionally, at least one strain gauge, shown in one place by item 59 in FIG. 1, may be mounted on any of the coupling rods 51, 52, or 55 or on the test specimen 72 to measure the static tensile force on the column assembly 50 which, correspondingly, is the same as the static tensile force on the test specimen 72.

The function of isolation masses 53a and 53b is to prevent vibrations of column assembly 50 from being transferred to the top beam 61 and to the moveable head 62 of test machine 60 and, in turn, to prevent any of the structural elements of test machine 60 from having an effect on the mechanical resonance behavior of the column assembly 50. By making each of the isolation masses approximately one order of magnitude greater than the mass of the dynamic actuator unit 80, only minor and negligible dynamic displacements of isolation masses 53a and 53b will occur.

Dynamic loading is provided by two piezoelectric actuator stacks 83a and 83b. Each stack 83a and 83b comprises polarized electrostrictive ceramic disks. More specifically, a number of piezoelectric ceramic disks, typically made from lead zirconate titanate material, are electroded on the their plane surfaces and polarized along the disk thickness dimension. Each stack is placed between the inner and outer faces of a cylindrical coupler 84. For reasons of mechanical symmetry and balanced actuator force generation as well as appropriate electrical connection of the piezoelectric disks, each piezoelectric stack is comprised of an identical even number of disks.

An example of a suitable piezoelectric actuator 83a or 83b is one having fourteen disks, with an assembled stack length of 0.742 inches. The disks are assembled in electrical parallel connection to provide relatively low-voltage actuation of dynamic mechanical-series displacements. A suitable maximum operating field within each disk might be 20 volts/mil. For example, a 0.050 inch thick plate could be excited by a maximum voltage of 1000 volts.

By means of this actuator 80 configuration, the entire combination of components comprising the column assembly 50 between isolation masses 53a and 53b may be caused to vibrate and thereby superimpose oscillatory dynamic forces onto the tensile forces already present in the column assembly 50. Under this dynamic operating condition, if the frequency of the AC electrical excitation voltage applied to piezoelectric actuator stacks 83a and 83b is varied from a low value to a high value, several mechanical resonances will occur in the column assembly 50. Each successive resonance will be associated with a specific effective combination of compliances and masses comprising the frequency-dependent complex mechanical impedance of the column assembly 50. In particular, since the coupling bar 82 and the coupling rods 51, 52, and 55, all of which are subject to strong dynamic vibrations, are all deliberately made stiffer than the test specimen 72, the lowest mechanical resonance of column assembly 50 will be governed primarily by the compliance of the test specimen 72 and an effective dynamic equivalent mass representing the net mechanical impedance of the other components of column assembly 50 at the particular resonance governed by specimen 72. Furthermore, when considered separately, the mechanical resonance frequency of the dynamic actuator unit 80 will be at a higher frequency than the specimen resonance frequency and will be governed primarily by the compliance of the coupling bar 82 and the masses of the attached actuator components 83a and 83b in combination with secondary effects introduced by the other components in the column assembly 50.

Piezoelectric actuators 83a and 83b work in opposition to each other to cause column assembly 50 to be in resonance. In other words, to excite the desired mechanical resonance governed by the test specimen, the electrical polarities of the AC voltages applied to piezoelectric actuator stacks 83a and 83b are such that the two stacks simultaneously and synchronously push and pull on coupling bar 82 and, thus, as a combined unit, dynamic actuator 80 also simultaneously and synchronously pulls and pushes on coupling rods 51 and 55 to introduce a strong dynamic force into those coupling rods 51 and 55 and into specimen holder 70. Moreover, since the test specimen 72 is the most compliant component in the column assembly 50, it will experience the largest dynamic strain of all elements of the column and this strain will have a maximum amplitude when the frequency of electrical excitation applied to dynamic actuator unit 80 corresponds to the mechanical resonance frequency of column assembly 50 determined by the compliance of test specimen 72.

Examples of suitable materials for constructing column assembly 50 are iron, titanium, and aluminum alloys for the structural elements and piezoelectric ceramic for the piezoelectric actuators 83a and 83b. Although several specific materials are identified herein as being suitable and are used as examples, other materials are also suitable. For example, various iron alloys may be used to permit higher stresses to be developed in the column assembly 50 or permit the design of a smaller test machine. Also, the dynamic stresses may be produced by any one of several types of piezoelectric materials and ceramic compounds. Furthermore, the dynamic stresses may be produced by means of a magnetostrictive material, through appropriate modification of the dynamic loading actuators 83a and 83b. In the case of a dynamic actuator made from magnetostrictive material, a set of rods with windings could be substituted for the piezoceramic stacks.

Fretting Fixture for Test Machine

As stated above, FIG. 1 includes an illustration of a fretting fixture 20, used as an accessory to column assembly 50. As stated above, column assembly 50, when mounted in a conventional test machine 60, is used for fatigue testing of prepared specimens made of selected materials to be subjected to stress testing. A particular type of stress, relevant to the present invention, is interface stress at surface-loaded contact points, such as between vibrating machine components. This stress can cause high-cycle material fatigue. The initial damage that occurs as a result of this stress is referred to as "fretting" damage. If persistent, fretting can result in surface cracking and failure of the components involved.

Fretting fixture 20 is used for inducing fretting fatigue damage. It is clamped to a specimen 72 in the manner described below.

FIGS. 2 and 3 are two views of fretting fixture 20. FIG. 2 is a front view, and FIG. 3 is a side view along line A—A of FIG. 1.

As stated above and as explained in additional detail below, fretting fixture 20 makes possible the generation of the interface shear forces necessary for fretting fatigue testing. In particular, test machine 60 and column assembly 50 act in combination to impart to the test specimen, simultaneously, a static force and a dynamic force, respectively, for controlled cyclic testing at vibrational rates in the frequency range of 1000–3000 Hz, depending on the test specimen size and material properties and the mass and the stiffness of the components of column assembly 50. Test machine 60 may impose static tensile loading on the specimen 72 at a force up to 6000 lbf and the dynamic operation of column assembly 50 may superimpose dynamic loading on the specimen at a double-amplitude oscillatory force up to 2400 lbf. Generation of the shear forces on specimen 72, through vibratory motions of the specimen holder unit 70, asymmetrical with respect to the center of the specimen 72, is made possible by the ability of the combined assembly to impart both a dynamic tensile loading vibration and a dynamic translation motion at the column assembly mechanical resonance cyclic rate.

Fretting fixture 20 is essentially comprised of a clamping frame 22, two inertial masses 23a and 23b, and a fretting piece 24. The test specimen 72 and the fretting piece 24 are positioned between the inertial masses 23a and 23b, and the entire fretting fixture 20 is clamped onto specimen 72 by means of clamping frame 22.

Frame 22 has two or more loading rods 22a, with a clamping beam 22b at each end. The ends of rods 22a extend through holes in clamping beams 22b, and may be threaded. This permits nuts 22c to be used to clamp the specimen 72 and fretting piece 24, positioned between the inertial masses 23a and 23b, against each other within frame 22.

When nuts 22c are tightened, clamping frame 22 imparts an adjustable static compressional loading force between fretting piece 24 and specimen 72. This static loading force is oriented normal to the surface of test specimen 72 and is an important quantitative parameter related to the interface stress conditions between fretting piece 24 and specimen 72 that result when specimen 72 undergoes oscillatory translation motion. Conventional strain gauge sensors 27 mounted on loading rods 22a are used to measure the normal force between the fretting piece and the specimen.

Inertial masses 23a and 23b are made from a high density material, such as a tungsten alloy. Masses 23a and 23b provide inertia for imparting the required shear force between specimen 72 and fretting piece 24. To achieve the transfer of the inertial reaction force of mass 23a to fretting piece 24 and thence to the contact point between the fretting piece 24 and the specimen 72, it should be understood that the inertial mass 23a and fretting piece 24 are rigidly attached together and thereby behave as a single combined mass. This inertial force, primarily imparted by mass 23a in reaction to the translation motions of specimen 72, is therefore the principal basis by which the shear forces and related fretting stresses are generated at the interface between the fretting piece and the specimen. The contact area between fretting piece 24 and specimen 72 is made sufficiently small to create compressional and shear forces of sufficient magnitude to cause fretting fatigue and subsequent fretting damage to the specimen as a result of long-duration cyclic testing. Mass 23b serves the function of providing a balancing inertial force, via a large-area non-fretting pad, on the opposite side of specimen 72 so that, in particular, the force between fretting piece 24 and specimen 72 is approximately a pure shear force at the fretting contact interface. The normal force imparted to fretting piece 24 at the shear-stressed interface is always adjusted to be at least sufficient but, in general, is made somewhat greater than necessary to prevent any sliding action between fretting piece 24 and specimen 72.

Fretting piece 24 has a material composition, a surface finish, a contact area, and a size and contour shape relative to specimen 72 that will result in fretting. Pad 25 acts as a counter-loading pad for the normal force that is applied to specimen 72 by clamping frame 20. Pad 25 is made from a non-fretting material such as a thin sheet of Teflon®. By making the fretting fixture 20 compact in size and high in mass, it represents a loading contact between the fretting piece 24 and the test specimen 72 such that fretting effects occur at a known and selected contact area. By making the fretting fixture 20 physically balanced and symmetrical with respect to the vibrational axis of the test specimen 72, through the use of inertial mass 23b and loading pad 25, extraneous vibrational modes (such as rocking motions at the fretting piece contact area) are avoided, thus providing well defined vibration conditions at the fretting contact position. Furthermore, by means of properly selected sensors and test machine materials, fretting testing can be performed.

Conventional strain gauges (or load cells) 27 and accelerometer 28 mounted on loading rods 22 and on inertial mass 23a, respectively, may be used to measure the loading force conditions at the fretting contact area during fretting tests. These devices permit the shear and normal forces at the fretting contact to be measured and adjusted as may be necessary to provide the proper combination of forces for fretting. Specifically, strain gauges 27 measure the normal force and accelerometer 28 measures the shearing force. Unlike other methods of fretting simulation, the static and dynamic forces associated with this fretting fixture 20 may be quantitatively measured and known. Additional instrumentation associated with column assembly 50 can be used to provide data on the oscillatory translational displacement motions of the test specimen, the cyclic vibrational frequency, and the accumulated number of vibration cycles during a given fretting test.

A computer (not shown) may be suitably programmed to handle control inputs for regulating both the static and dynamic stresses in the test specimen and its dynamic translational displacements as well as to record these and other test parameters. The computer may be any general purpose personal or desktop computer, such as are commercially available. It may have appropriate interfaces for receiving input signals from strain gauges 27 and accelerometer 28, which are attached to fretting device 20 as well as from acceleration sensor 59 and strain gauge sensor 57 on column assembly 50.

In the mode of operation described above, the lower end of test specimen 72, shown in FIG. 1, will undergo a substantial oscillatory translational displacement and extensional strain relative to its upper end. This dynamic displacement is the desired mechanical condition for applying the fretting fixture 20, described earlier and illustrated in FIGS. 2 and 3, to the test specimen. For this purpose, the fretting fixture 20 is attached to test specimen 72 in the same manner discussed earlier, namely, by clamping it at the midpoint of specimen 72 such that it is freely supported by the specimen 72. This clamping action places the fretting piece 24, also shown in FIGS. 2 and 3, in pressure contact with specimen 72 to provide a desired and measurable normal force at the point of contact. When the dynamic actuator unit 80 of the column assembly 50 is excited at the mechanical resonance governed by the test specimen, that is, at the principal resonance of column assembly 50, the test specimen 72 undergoes oscillatory translation motions and, thereby, causes a dynamic shear force to be produced at the point of contact of fretting piece 24 and specimen 72. This dynamic shear force is measurable by acceleration sensor 28 attached to inertial mass 23a, shown in FIG. 2.

By selecting the size and materials of the components comprising the column assembly 50, the mechanical resonance frequency of the column system may be adjusted to fall in the general range of about 1000–3000 Hz, depending on the physical characteristics of specimen 72. For example, one convenient method of adjusting this principal resonance is to make the coupling rod 55 from stainless steel and to make its length and/or diameter such that the desired resonance frequency is achieved. Both of the dimensional parameters mentioned affect the mechanical stiffness of the rod, and this stiffness, in turn, has a direct effect on the net complex mechanical impedance of the column assembly 50, and thereby a corresponding effect on the principal resonance frequency. Thus, by experimentally modifying coupling rod 55, the principal resonance of the column assembly 50 may be adjusted to a desired value for conducting either high-cycle fatigue tests or fretting fatigue tests. In particular, lengthening or reducing the diameter of coupling rod 55 will shift the principal resonance down in frequency whereas making the length shorter or the diameter larger will shift the principal resonance up in frequency.

The fretting fixture testing system illustrated in FIG. 1 includes sensor components attached to both the fretting fixture 20 and, for example, to the specimen holder grip component 71b to provide quantitative measurements and signals to indicate the oscillatory translation displacement of the end of the gauge section of specimen 72 held in grip component 71b. This latter signal also contains information on the amplitude and frequency of the mechanical resonance as governed by the test specimen 72. In addition to these dynamic sensor signals, the static tensile force is obtained either as a signal from a strain gauge 57 attached to column assembly 50, for example, on coupling rod 55, or directly as a readout from the test machine 60. Computer control of the dynamic actuator unit 80 and the test machine 60 may be achieved as described above by tracking the mechanical resonance frequency of the column assembly 50 and the static loading force and adjusting the amplitude and frequency of the exciter signal and the test machine tensile force, respectively, to automatically maintain the desired test conditions.

Other Embodiments

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A column assembly for use with a fatigue test machine and for applying dynamic loading to a test specimen, the test machine having a frame into which a the column assembly may be mounted, the column assembly comprising:
   a series of column assembly elements, arranged along a common axis in the following series:
   a first isolation mass;
   an upper specimen grip;
   a lower specimen grip;
   wherein the upper and lower specimen grip are spaced apart such that a test specimen may be mounted between them;
   a dynamic actuator unit having a first dynamic actuator and a second dynamic actuator, wherein the dynamic actuator unit is located such that both the first dynamic actuator and the second dynamic actuator are operable to apply vibration to the same side of the test specimen; and
   a second isolation mass;
   wherein the location of the dynamic actuator unit relative to the first isolation mass and second isolation mass results a dynamic actuator unit that is operable to apply mechanical vibrations that are asymmetric relative to the test specimen.

2. The column assembly of claim 1, wherein the dynamic actuators are piezoelectric actuators.

3. The column assembly of claim 2, wherein each piezoelectric actuator comprises a stack of piezoelectric disks.

4. The column assembly of claim 1, wherein the dynamic actuators are magnetostrictive actuators.

5. The column assembly of claim 1, wherein each isolation mass has a mass that is approximately one order of magnitude greater than the mass of one of the dynamic actuator units.

6. The column assembly of claim 1, wherein the first and second isolation masses and the first and second dynamic actuators are coupled along the common axis with coupling rods.

7. The column assembly of claim 6, wherein the coupling rods each are made from a material having greater stiffness than that of the specimen.

8. The column assembly of claim 1, wherein the center of mass of the column assembly is displaced from the midpoint of the column assembly.

9. The column assembly of claim 1, wherein the first and second specimen grips are displaced from the midpoint of the column assembly.

10. A column assembly for use with a fatigue test machine and for applying dynamic loading to a test specimen, the test machine having a frame into which a the column assembly may be mounted, the column assembly comprising:
    a first isolation mass;
    a first coupling rod for connecting the isolation mass to the upper portion of the test machine frame;
    an upper specimen grip;
    a second coupling rod for connecting the upper specimen grip to the isolation mass;
    a lower specimen grip;
    wherein the upper and lower specimen grip are spaced apart such that a test specimen may be mounted between them;
    a dynamic actuator unit having a first dynamic actuator and a second dynamic actuator, wherein the dynamic actuator unit is located such that both the first dynamic actuator and the second dynamic actuator are operable to apply vibration to the same side of the test specimen;
    a fourth coupling rod for connecting the first dynamic actuator to the lower specimen grip;
    a second dynamic actuator;
    a fifth coupling rod between the first dynamic actuator and the second dynamic actuator, such that the dynamic actuators are directly coupled;
    a second isolation mass;
    wherein the location of the dynamic actuator unit relative to the first isolation mass and second isolation mass results a dynamic actuator unit that is operable to apply mechanical vibrations that are asymmetric relative to the test specimen;
    a sixth coupling rod for connecting the second isolation mass to the second dynamic actuator; and
    a seventh coupling rod for connecting the second isolation mass to the lower portion of the test machine frame.

11. A method of using a fatigue test machine to impart fatigue stresses in a test specimen, the fatigue test machine having a frame into which a column assembly may be mounted, comprising the steps of:
    mounting a column assembly into the frame, the column assembly having the following components arranged along a common axis in series: a first isolation mass, a specimen holder, a dynamic actuator unit, and a second isolation mass;
    wherein the specimen holder has two opposing faces spaced apart by an air gap into which a test specimen may be attached;
    wherein the dynamic actuator unit has a first dynamic actuator and a second dynamic actuator operable to apply vibration to the same side of the test specimen;
    attaching a test specimen between opposing faces of the specimen holder; and
    activating the dynamic actuators by time varying activation signals, such that they apply mechanical vibrations that are asymmetric relative to the test specimen.

12. The method of claim 11, further comprising the step of using the test machine to apply static tensile stress to the specimen.

13. The method of claim 11, further comprising the step of adjusting the frequency of activation of the dynamic actuators such that it substantially corresponds to the mechanical resonance frequency of the test specimen.

14. The method of claim 11, further comprising the step of sensing the frequency of oscillation of the column assembly and controlling the activation signal in response to the sensing step.

15. The method of claim 11, further comprising the step of selecting the size and materials of the elements of the column assembly such that the resonance frequency of the column assembly falls within the range of 1000–3000 hz.

16. The method of claim 11, further comprising the step of placing a coupling rod between the second dynamic actuator and the second isolation mass, and of modifying the dimensions of the coupling rod to achieve a given resonance frequency of the column assembly.

* * * * *

UNITED STATES PATENT AND TRADEMARK OFFICE
CERTIFICATE OF CORRECTION

PATENT NO. : 6,813,960 B1
DATED : November 9, 2004
INVENTOR(S) : Thomas E. Owen et al.

It is certified that error appears in the above-identified patent and that said Letters Patent is hereby corrected as shown below:

Column 7,
Line 36, please delete "a" before "the".

Column 8,
Line 42, please insert -- in -- between "results" and "a dynamic".

Signed and Sealed this

First Day of March, 2005

JON W. DUDAS
*Director of the United States Patent and Trademark Office*